United States Patent [19]

Kurihara et al.

[11] Patent Number: 5,176,937
[45] Date of Patent: Jan. 5, 1993

[54] REINFORCER FOR TASTE-MODIFIER

[75] Inventors: Yoshie Kurihara, 4-7, Okuzawa 7-chome, Setagaya-ku, Tokyo 125; Hiroshige Kohno, Tokyo; Masaaki Kato, Tokyo; Kenji Ikeda, Tokyo; Masako Miyake, Tokyo, all of Japan

[73] Assignees: Yoshie Kurihara; Asahi Denka Kogyo Kabushiki Kaisha, both of Tokyo, Japan

[21] Appl. No.: 649,373

[22] Filed: Jan. 31, 1991

Related U.S. Application Data

[63] Continuation of Ser. No. 362,861, Jun. 7, 1989, abandoned.

[30] Foreign Application Priority Data

Jun. 21, 1988 [JP] Japan .................. 63-153143
Nov. 2, 1988 [JP] Japan .................. 63-277717
Nov. 17, 1988 [JP] Japan .................. 63-290832

[51] Int. Cl.⁵ ............................. A23L 1/221
[52] U.S. Cl. ........................ 426/655; 426/548; 426/615; 426/638; 426/650; 426/534; 426/627; 426/640
[58] Field of Search ............ 426/548, 615, 638, 650, 426/534, 655, 627, 640

[56] References Cited

U.S. PATENT DOCUMENTS 4,612,205 9/1986 Kupper et al. .............. 426/599
4,758,351 7/1988 Kern ...................... 426/271 X

FOREIGN PATENT DOCUMENTS 0003911 9/1979 European Pat. Off.
2089624 1/1972 France.
2315864 1/1977 France.
1506052 4/1978 United Kingdom.
2185674 7/1987 United Kingdom.

OTHER PUBLICATIONS

G. Penso: "Index Plantarum Medicinalium Totius Mundi Eorumque Synomymorum", 1984, O.E.M.F., Milano, IT *p. 294, lines 31–36.
Commonwealth Agricultural Bureau, abstract 0206272, 7C010-01239, OC054-06355m 7W010-01239, Lim-Ho, Chee Len: "Tissue culture of *Curculigo latifolia* dry. ex W. T. Ait (Hypoxidaceae)" & Gardens' Bulletin, 1981, 34(2), *Abstract*.
Chemical Abstracts, vol. 107, 1987, p. 455, abstract 194889t, Columbus, Ohio, US J. Xu et al.: "Chemical constituents of Xianmao (*Curculigo Orchioides*), I. Isolation and characterization of *curculigine A*" & Zhongcaoyao, 1987, 18(5), 194–5, 222 *Abstract*.

*Primary Examiner*—Joseph Golian
*Attorney, Agent, or Firm*—Frishauf, Holtz, Goodman & Woodward

[57] ABSTRACT

A reinforcer for a taste-modifier comprising fresh *Curuculigo latifolia* fruits, dried fruits thereof or a curuculin-containing material obtained therefrom, which comprises a material capable of lowering the concentration of divalent metal ions in the mouth and reinforces the taste-modification effect of said taste-modifier.

6 Claims, No Drawings

REINFORCER FOR TASTE-MODIFIER

This application is a continuation of application Ser. No. 07/362.861, filed Jun. 7, 1989 (abandoned).

BACKGROUND OF THE INVENTION

1. Field of the Invention

This invention relates to a reinforcer for a taste-modifier. More particularly, it relates to a reinforcer for a taste-modifier comprising fresh *Curculigo latifolia* fruits, dried fruits thereof or a curuculin-containing material obtained therefrom, which reinforces the taste-modification effect of said taste-modifier by lowering the concentration of divalent metal ions in the mouth.

2. Description of the Prior Art

Known taste-modifiers, which affect the receptor membranes on the tongue in such a manner as to modify the taste of a food, include those which remove the sweetness of a sweet food in the mouth, for example, gymnemic acid contained in *Gymnema sylvestre* leaves and ziziphine contained in *Ziziphus jujuba* leaves; and those which convert the sourness of a sour food into sweetness in the mouth, for example, miraculin contained in *Synsepulm dulcificum* fruits.

It is further known that *Curculigo latifolia* fruits. which grow in Western Malaysia and the southern part of Thailand and belong to the genus Curculigo of Amaryllidaceae, are good to eat and exhibit an appetizing effect.

Although miraculin has the abovementioned effect, it is not put into practical use as a taste-modifier because of its poor stability.

No effect of *Curculigo latifolia* fruits except the abovementioned one has been known so far.

The present inventors have found that a sour material or water taken after eating *Curculigo latifolia* fruits would taste sweet. Thus they have attempted to identify the sweetness-inducer. As a result, they have found that a specific protein contained in *Curculigo latifolia* fruits is the aimed sweetness-inducer (cf. Japanese Patent Application No. 153143/1988).

However the taste-modification effect of the abovementioned curuculin-containing taste-modifier is to such an extent at the highest that a sweetness comparable to that of a 0.3M aqueous solution of sucrose may be induced from a 0.02M aqueous solution of citric acid or that a sweetness comparable to that of a 0.1M aqueous solution of sucrose may be induced from water, when the receptor membrane on the tongue is fully modified with a sufficient amount of said taste-modifier. Thus the industrial application range of said taste-modifier containing curuculin is restricted thereby.

SUMMARY OF THE INVENTION

It is an object of the present invention to provide a reinforcer for the abovementioned curuculin provide a reinforcer for the abovementioned curuculin-containing containing taste-modifier which can reinforce the taste-modification effect of said taste-modifier and thus enlarge the application range of the same.

As a result of extensive studies, the present inventors have succeeded in achieving the above object with the use of a material capable of lowering the concentration of divalent metal ions in the mouth.

Accordingly the present invention, which has been completed based on the above finding, provides a reinforcer for a taste-modifier comprising fresh *Curculigo latifolia* fruits, dried fruits thereof or a curuculin-containing material obtained therefrom, which comprises a material capable of lowering the concentration of divalent metal ions in the mouth.

The reinforcer for a taste-modifier of the present invention would reinforce the taste-modification effect of the taste-modifier comprising fresh *Curculigo latifolia* fruits, dried fruits thereof or a curuculin-containing material obtained therefrom and thus enlarge the industrial application range of the same. Therefore it is highly effective and important in order to put said taste-modifier into practical use.

DETAILED DESCRIPTION OF THE INVENTION

A typical example of divalent ions in the mouth is calcium ion contained in the saliva. Further magnesium and ferrous ions may be cited therefor.

Examples of a material capable of lowering the concentration of these metal ions include those containing carbonate ions, those capable of forming carbonate ions in the mouth and cation exchangers.

A carbonate ion would react with a calcium or magnesium ion to thereby form a precipitate comprising a water-insoluble salt. Consequently it would lower the concentration of the calcium and magnesium ions in the mouth. Examples of the materials containing carbonate ions or forming the same in the mouth include carbon dioxide gas, water soluble carbonates and aqueous solutions thereof. Examples of the water soluble carbonates include sodium hydrogencarbonate and potassium carbonate.

The abovementioned aqueous solutions of carbon dioxide gas or water soluble carbonates preferably have a carbonate ion concentration of 0.01 to 1.0M.

Examples of the cation exchangers include ion exchange resins such as Amberlite IR-120 and IRC-50 (mfd by Rohm and Haas), Dowex 50 (mfd. by Rohm and Hass) and Bio-Rex 70 (mfd. by Rohm and Haas), ion exchange celluloses such as CM-cellulose and phosphocellulose and CM-Sephadex.

The reinforcer of the present invention comprising a material capable of lowering the concentration of divalent metal ions in the mouth may be administered into the mouth. When the reinforcer of the present invention comprising the abovementioned cation exchanger is to be introduced into the mouth, it may be preferably come into contact with the upper surface of the tongue.

The reinforcer of the present invention may be taken either before taking the taste-modifier comprising fresh *Curculigo latifolia* fruits, dried fruits thereof or a curuculin-containing material obtained therefrom or thereafter. When said reinforcer is to be administered after taking the taste-modifier, it may be taken either after taking the material to be modified, such as a sour material, or simultaneously therewith.

The fresh *Curculigo latifolia* fruits or dried fruits thereof constituting the taste-modifier to be used in the present invention may be preferably free from peels and seeds, since no curuculin is contained in these parts.

The method for drying *Curculigo latifolia* fruits is not particularly restricted. Namely, sun-dried *Curculigo latifolia* fruits, hot air-dried ones and lyophilized ones such as lyophilized pulp may be used in the present invention.

The fresh *Curculigo latifolia* fruits or dried fruits thereof may be generally ground, milled or pasted prior to the use, though the form of the fresh *Curculigo lati-*

*folia* fruits or dried fruits thereof is not particularly restricted.

Examples of the curuculin-containing material obtained from fresh *Curculigo latifolia* fruits or dried fruits thereof described above include curuculin extracted from fresh *Curculigo latifolia* fruits, dried fruits thereof or the residue obtained by appropriately treating the fresh *Curculigo latifolia* fruits or dried fruits thereof and removing a curuculin-free component therefrom. The concentration of the curuculin extracted from fresh *Curculigo latifolia* fruits or dried fruits thereof is not particularly restricted. Namely, either a highly pure curuculin or an extract containing a large amount of materials other than the curuculin may be used in the present invention. Further the extract may be mixed with other components.

The extraction of the curuculin is not particularly restricted. A preferable example thereof comprises extracting from fresh *Curculigo latifolia* fruits or dried fruits thereof with an aqueous solution of a salt at a concentration of at least 0.01M. Examples of the salt include chlorides such as sodium chloride, potassium chloride, calcium chloride, magnesium chloride and ammonium chloride; phosphates such as sodium phosphate, potassium phosphate, magnesium phosphate and ammonium phosphate; carbonates such as sodium carbonate, potassium carbonate, magnesium carbonate and ammonium carbonate; sulfates such as sodium sulfates, magnesium sulfate, calcium sulfate and ammonium sulfate; sulfites such as sodium sulfite, magnesium sulfite, calcium sulfite and ammonium sulfite; nitrates such as sodium nitrate and potassium nitrate; nitrites such as sodium nitrite and potassium nitrite; lactates such as sodium lactate and calcium lactate; alum; burnt alum; sodium acetate; pyrophosphates such as sodium pyrophosphate and potassium pyrophosphate; propionates such as sodium propionate and calcium propionate; sodium benzoate; sodium fumarate; and sodium polyacrylate.

A typical example of the extraction of curuculin with the aqueous solution of a salt may be carried in the following manner.

An aqueous solution of a salt such as sodium chloride is added to fresh *Curculigo latifolia* fruits or dried fruits thereof and the obtained mixture is homogenized followed by filtering and centrifuging. Since curuculin is contained in the water-insoluble part of *Curculigo latifolia* sarcocarp, it is preferable to homogenize the above mixture of the fresh *Curculigo latifolia* fruits or dried fruits thereof and water followed by thoroughly washing the mixture to thereby remove the water-soluble part and extracting from the residue with the above-mentioned salt solution so as to elevate the purity of curuculin.

The concentration of the salt of the aqueous solution to be used for the extraction should be 0.01M or more, since curuculin can not be sufficiently extracted with a salt solution of a concentration lower than 0.01M. On the other hand, a salt solution of an excessively high concentration requires a prolonged period of time for desalting following the extraction. Thus the concentration of the salt solution preferably ranges from 0.1 to 1.0M, from the viewpoints of the extraction efficiency and the subsequent purification procedure.

The extract thus obtained with the use of the salt solution is then desalted and dried to thereby give a curuculin-containing material which is sufficiently available in practice. However the purity of curuculin can be further elevated by purifying the above extract by ion exchange chromatography with the use of CM-Sepharose and HPLC with the use of a gel column followed by desalting and drying. Thus pure curuculin can be obtained. It is a matter of course that the curculin purity may be further elevated by various purification procedures other than those described above, for example, known protein purification procedures such as salting-out or solvent precipitation.

A typical example of the curuculin thus obtained is a protein having a molecular weight of approximately 12,500 dalton, an amino acid residue number of 97 and an iso-electric point of 7.1. This protein is present as a dimer of a molecular weight of approximately 26,000 dalton. The following Table 1 shows the amino acid composition of this protein. Thus it contains relatively large amounts of aspartic acid, leucine and glycine.

TABLE 1

| Amino acid | | Amino acid composition | |
|---|---|---|---|
| | | % by mol | No. of residues |
| Aspartic acid | (Asp) | 17.3 | 17 |
| Threonine | (Thr) | 6.4 | 6 |
| Serine | (Ser) | 7.0 | 7 |
| Glutamic acid | (Glu) | 7.2 | 7 |
| Proline | (Pro) | 1.2 | 1 |
| Glycine | (Gly) | 12.5 | 12 |
| Alanine | (Ala) | 5.3 | 5 |
| Cystine | (Half-cys) | — | — |
| Valine | (Val) | 6.8 | 7 |
| Methionine | (Met) | 0.4 | 1 |
| Isoleucine | (Ile) | 4.2 | 4 |
| Leucine | (Leu) | 14.5 | 14 |
| Tyrosine | (Tyr) | 5.2 | 5 |
| Phenylalanine | (Phe) | 1.3 | 1 |
| Lysine | (Lys) | 2.7 | 3 |
| Histidine | (His) | 2.4 | 2 |
| Arginine | (Arg) | 5.5 | 5 |
| Total | | | 97 |

To further illustrate the present invention, the following examples will be given.

EXAMPLE 1

1 g of a *curculigo latifolia* fruit was finely ground in a mortar to thereby give a pasty taste-modifier.

The inside of the mouth was thoroughly washed with carbonated water and then 0.5 g of the above taste-modifier was made to uniformly adhere onto the upper surface of the tongue. One minute thereafter, 20 ml of a 0.02M aqueous solution of citric acid was kept in the mouth. Thus the citric acid solution showed a sweetness comparable to that of a sugar solution.

EXAMPLE 2

600 ml of water was added to 30 g of hot air-dried *curculigo latiofolia* fruits and the mixture was homogenized in a mixer for two minutes and centrifuged at 10,000 rpm for 30 minutes. After removing the supernatant which was colored, 600 ml of water was added to the residue. The obtained mixture was homogenized and centrifuged and the supernatant was removed. This procedure was repeated four times until noncolored supernatant was obtained.

To the residue thus obtained, was added 250 ml of 0.5M aqueous solution of NaCl. The mixture was homogenized in a mixer for two minutes and filtered under reduced pressure. 250 ml of 0.5M aqueous solution of NaCl was further added to the residue and the obtained mixture was homogenized and filtered under reduced pressure to thereby give a filtrate.

These filtrates were combined and centrifuged at 30.000 rpm for one hour. Thus a crude curuculin extract was obtained as the supernatant.

This crude extract was desalted and dried to thereby give a curuculin-containing material, namely, crude curuculin.

100 mg of the crude curuculin thus obtained and 1 mg of sodium chloride were dissolved in 20 ml of water to thereby give a 0.5% aqueous solution of the crude curuculin.

1 ml of this curuculin solution was kept in the mouth for a minute and then expectorated. Subsequently 5 mg of L-ascorbic acid or a mixture of L-ascorbic acid and sodium hydrogencarbonate (1:1) was taken. Table 2 shows the sweetness induced in each case.

TABLE 2

| Sample | Sweetness |
|---|---|
| L-ascorbic acid | Comparable to that of 0.2 M aqueous solution of sucrose |
| L-ascorbic acid/ sodium hydrogencarbonate (1:1) | Comparable to that of 0.3 M aqueous solution of sucrose |

EXAMPLE 3

500 ml of the crude curuculin extract obtained in Example 2 was concentrated to 30 ml through ultrafiltration. Then 70 ml of a 0.01M phosphate buffer (pH 6.8) was added thereto to thereby give the total volume of 100 ml. The sample solution thus obtained was passed through a column charged with CM-Sepharose CL-4B which had been equilibrated with a 0.01M phosphate buffer (pH 6.8) (bed volume: 130 ml, bed height: 17 cm). After washing with a 0.01M phosphate buffer (pH 6.8), the column was subjected to gradient elution with 0 to 1.0M NaCl/0.01M phosphate buffer (pH 6.8) and active fractions were combined. These active fractions were concentrated by ultrafiltration, subjected to HPLC with the use of a gel column charged with TSK Gel G3000SW (mfd. by Toyo Soda Mfg. Co., Ltd.) and eluted with a 0.01M phosphate buffer (pH 6.8).

Thus curuculin was eluted as a sharp peak showing an intense activity.

This active fraction was desalted and dried to thereby give purified curuculin.

10 mg of the purified curuculin thus obtained and 1 mg of sodium chloride were dissolved in 20 ml of water to thereby give a 0.01% aqueous solution of curuculin.

A cation exchange resin Amberlite IR-120 (mfd. by Rohm and Haas) was kept in the mouth for a minute to thereby uniformly contact it with the whole upper surface of the tongue. Then it was expectorated. Subsequently 1 ml of the 0.01% aqueous solution of curuculin obtained above was kept in the mouth for a minute and then expectorated. Then a 0.02M aqueous solution of citric acid was taken. Table 3 shows the sweetness thus induced and that induced by the same procedure as the one described above except no cation exchange resin was used.

TABLE 3

| Cation exchanger | Sweetness |
|---|---|
| No | Comparable to that of 0.3 M aqueous solution of sucrose |
| Yes | Comparable to that of 0.4 M aqueous solution of sucrose |

What is claimed is:

1. A reinforcer for a taste-modifier comprising a salt solution extract of fresh *Curculigo latifolia* fruits, or dried fruits thereof, said reinforcer comprising a material capable of lowering the concentration of divalent metal ions in the mouth, said material being selected from the group consisting of carbon dioxide gas, water soluble carbonates; 0.01 to 1.0M aqueous solutions of carbon dioxide gas or said carbonates, and cation exchangers, and reinforces the taste-modification effect of said taste-modifier when said taste-modifier modifies the material to be modified.

2. The reinforcer of claim 1 wherein the material is said cation exchanger.

3. The reinforcer of claim 1 wherein said material is said carbonate.

4. The reinforcer of claim 1 wherein said material is said carbon dioxide gas.

5. The reinforcer of claim 1 wherein the material is said aqueous solution of carbon dioxide gas.

6. The reinforcer of claim 1 wherein the material is said aqueous solution of said carbonate.

* * * * *